(12) United States Patent
Hsu

(10) Patent No.: US 11,934,014 B1
(45) Date of Patent: Mar. 19, 2024

(54) COLOR-LIGHT GENERATION SYSTEM AND METHOD OF USING THE SAME

(71) Applicant: FU JEN CATHOLIC UNIVERSITY, New Taipei (TW)

(72) Inventor: Jin-Cherng Hsu, New Taipei (TW)

(73) Assignee: FU JEN CATHOLIC UNIVERSITY, New Taipei (TW)

( * ) Notice: Subject to any disclaimer, the term of this patent is extended or adjusted under 35 U.S.C. 154(b) by 0 days.

(21) Appl. No.: 17/978,223

(22) Filed: Nov. 1, 2022

(51) Int. Cl.
*G02B 6/35* (2006.01)
*G02B 5/18* (2006.01)

(52) U.S. Cl.
CPC ........ *G02B 6/3546* (2013.01); *G02B 5/1861* (2013.01); *G02B 6/3512* (2013.01); *G02B 6/356* (2013.01)

(58) Field of Classification Search
None
See application file for complete search history.

(56) References Cited

U.S. PATENT DOCUMENTS

| | | | | |
|---|---|---|---|---|
| 11,513,350 | B2* | 11/2022 | Waldern | G02B 27/0081 |
| 2003/0223748 | A1* | 12/2003 | Stowe | H04Q 11/0005 |
| | | | | 398/48 |
| 2004/0252938 | A1* | 12/2004 | Ducellier | G02B 6/12033 |
| | | | | 385/27 |
| 2005/0002600 | A1* | 1/2005 | Ducellier | H04Q 11/0005 |
| | | | | 385/24 |
| 2005/0036202 | A1* | 2/2005 | Cohen | G02B 6/272 |
| | | | | 359/489.05 |
| 2006/0078251 | A1* | 4/2006 | Ducellier | G02B 6/29307 |
| | | | | 385/24 |
| 2008/0239441 | A1* | 10/2008 | Aota | G02B 6/29313 |
| | | | | 359/212.1 |
| 2008/0273834 | A1* | 11/2008 | Barbarossa | G02B 6/356 |
| | | | | 385/20 |
| 2008/0298424 | A1* | 12/2008 | Khan | H04N 9/3161 |
| | | | | 372/107 |
| 2011/0217037 | A1* | 9/2011 | Yoshida | G02B 6/356 |
| | | | | 398/48 |

(Continued)

FOREIGN PATENT DOCUMENTS

TW 202222243 6/2022

OTHER PUBLICATIONS

"Office Action of Taiwan Counterpart Application", dated Apr. 10, 2023, p. 1-p. 8.

*Primary Examiner* — Jerry Rahll
(74) *Attorney, Agent, or Firm* — JCIPRNET

(57) ABSTRACT

A color-light generation system includes a light source emitting first and second area light beams, a reflective grating receiving the first and second area light beams and then generating first and second area reflected light beams, an array optical switch including first and second areas receiving the first and second area reflected light beams respectively, a light mixer including a light mixer first area and a light mixer second area receiving a light beam from the first area and a light beam from the second area respectively, and a controller electrically connected to the array optical switch and controlling the array optical switch, so that the light mixer first area outputs a first color light, and the light mixer second area outputs a second color light. A method of using the system is also provided.

12 Claims, 5 Drawing Sheets

(56) References Cited

U.S. PATENT DOCUMENTS

| | | | | |
|---|---|---|---|---|
| 2012/0002917 A1* | 1/2012 | Colbourne | ............ | G02B 6/356 385/17 |
| 2020/0292840 A1* | 9/2020 | Popovich | ............ | G02B 6/0016 |
| 2020/0341194 A1* | 10/2020 | Waldern | ............ | G02F 1/13342 |

* cited by examiner

COLOR-LIGHT GENERATION SYSTEM AND METHOD OF USING THE SAME

BACKGROUND

Technical Field

The disclosure relates to a color-light generation system and a method of using the same.

Description of Related Art

Generally speaking, there are three types of cone cells in the retina of the human eye, which are respectively used to sense the light of the three primary colors (red, green, and blue). A problem in the cone cells will affect the eye's ability to sense color, so patients with such a problem may have a weaker ability to identify certain colors and feel that different colors look similar.

However, the current inspection method for color blindness relies solely on the assistance of the professionals, and therefore there are some problems such as operational difficulty, time-consumingness, reliance on manual transfer for data retrieval, and digitalization or automation difficulty. Moreover, test subjects are prone to eye fatigue as a result of the prolonged inspection time, which leads the inspection result to deviate greatly.

SUMMARY

The disclosure provides a color-light generation system and a method of using the same, which inspect a test subject's ability to distinguish a color simply, and the system and the method of using the system are further simplified.

An embodiment of the disclosure provides a color-light generation system, which includes a light source, a reflective grating, an array optical switch, a light mixer, and a controller. The light source is configured to emit a first area light beam and a second area light beam. The reflective grating is configured to receive the first area light beam and the second area light beam and then generate a first area reflected light beam and a second area reflected light beam. The array optical switch includes a first area and a second area. The first area and the second area are configured to receive the first area reflected light beam and the second area reflected light beam, respectively. The light mixer includes a light mixer first area and a light mixer second area. The light mixer first area and the light mixer second area are configured to receive a light beam from the first area and a light beam from the second area, respectively. The controller is electrically connected to the array optical switch. The controller controls the array optical switch, so that the light mixer first area outputs a first color light, and the light mixer second area outputs a second color light.

An embodiment of the disclosure provides a method of using a color-light generation system, which includes the following. A first area light beam and a second area light beam are emitted by a light source. After the first area light beam and the second area light beam are received by a reflective grating, a first area reflected light beam and a second area reflected light beam are generated. The first area reflected light beam and the second area reflected light beam are received by a first area and a second area of an array optical switch, respectively. A light beam from the first area and a light beam from the second area are received by a light mixer first area and a light mixer second area of a light mixer, respectively. The array optical switch is controlled by a controller, so that a first color light is output by the light mixer first area, and a second color light is output by the light mixer second area.

Based on the above, in the color-light generation system and the method of using the same in the embodiment of the disclosure, the array optical switch is designed to include the first area and the second area, and the light mixer first area and the light mixer second area output the first color light and the second color light corresponding to the first area and the second area, respectively. Therefore, compared to a color-light generation system that is integrated using multiple sets of color generators, the color-light generation system and the method of using the same of the embodiment of the disclosure reduce the number of optical elements used in the system, which leads to a reduced cost.

DESCRIPTION OF THE EMBODIMENTS

Figure 1:
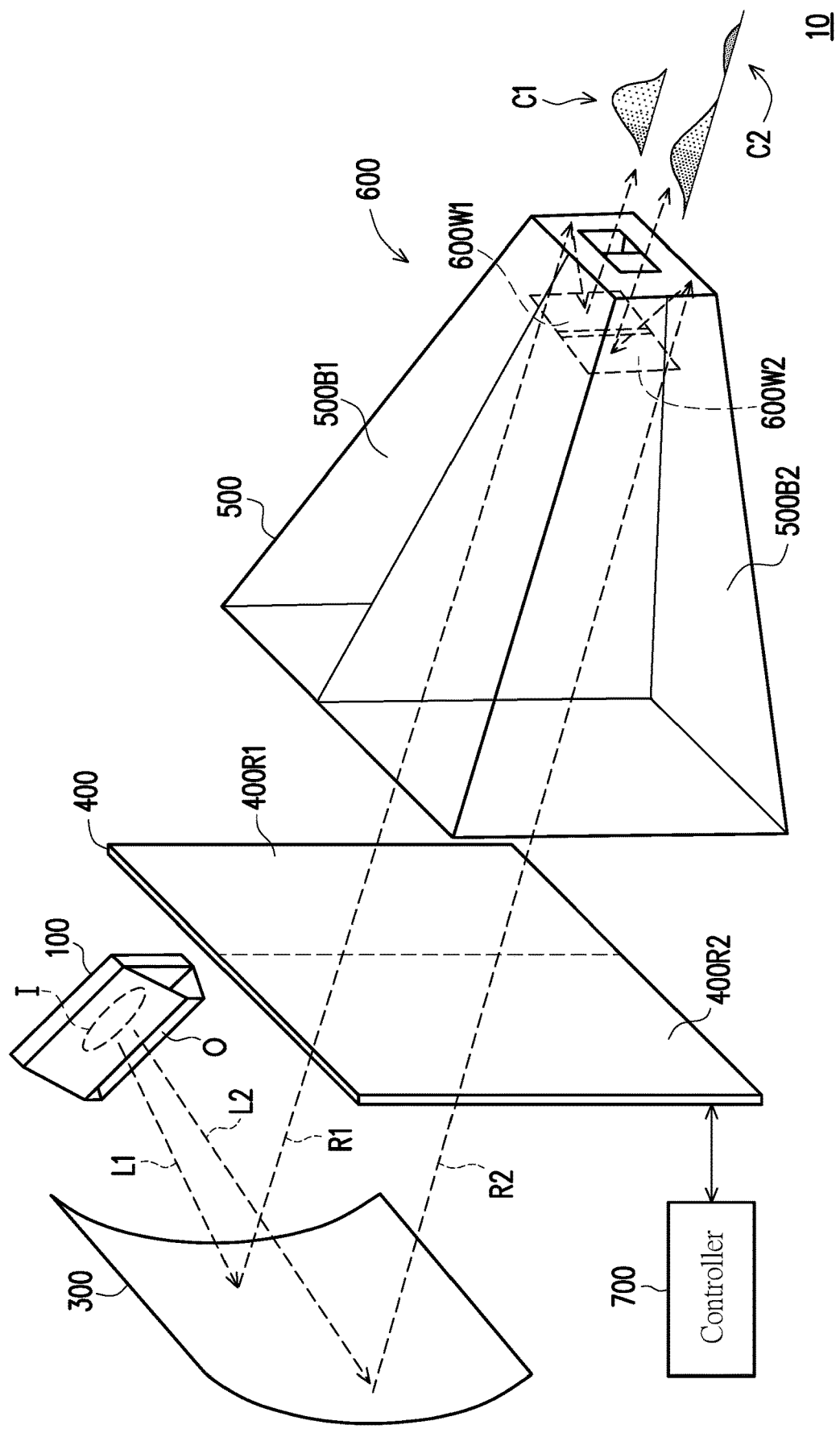
FIG. 1 is a schematic diagram of a color-light generation system according to an embodiment of the disclosure.

FIG. 1 is a schematic diagram of a color-light generation system according to an embodiment of the disclosure. Referring to FIG. 1, an embodiment of the disclosure provides a color-light generation system 10, which includes a light source 100, a reflective grating 300, an array optical switch 400, a light mixer 500, a diffusion sheet 600, and a controller 700.

In the embodiment, the light source 100 is configured to emit a first area light beam L1 and a second area light beam L2. The light source 100 may be a xenon lamp, a fluorescent lamp, an incandescent lamp, a light-emitting diode, a laser diode, or a combination thereof, but the disclosure is not limited thereto. In a preferred embodiment, the light source 100 is a D65 type solar light source, that is, a standard light source with a color temperature of 6500 K and a color rendering rate greater than or equal to 98%. Also, in an embodiment, the light source 100 may be a fiber optic light source.

In the embodiment, the reflective grating 300 is configured to receive the first area light beam L1 and the second area light beam L2 and then generate a first area reflected light beam R1 and a second area reflected light beam R2. When a light beam with a wave length range is incident on the reflective grating 300, the reflective grating 300 converts the light beam into multiple split light beams, and the split light beams are projected by the reflective grating 300 at multiple different angles based on the respective wave length of the split beams. In addition, in the embodiment, the reflective grating 300 may be a concave grating. Since the color-light generation system 10 uses the reflective grating 300, the optical path in the system is more flexible in design, so the system volume is further reduced.

In the embodiment, the array optical switch 400 includes a first area 400R1 and a second area 400R2. The first area 400R1 and the second area 400R2 are configured to receive the first area reflected light beam R1 and the second area reflected light beam R2, respectively. The array optical switch 400 may be a liquid crystal optical switch, a liquid crystal on silicon-spatial light modulator (LCoS-SLM), a spatial light modulator (SLM), or a digital micromirror device (DMD), but the disclosure is not limited hereto. The array optical switch 400 may be a two-dimensional array optical switch. Taking the array optical switch 400 of FIG. 1 as an example, when the aforementioned split light beams are incident on different positions of the array optical switch 400 at different angles, the array optical switch 400 is controlled to turn on a part of the optical switch, so that the light beam incident on the corresponding position of the optical switch that is turned on passes through.

In the embodiment, the light mixer 500 is divided into a light mixer first area 500B1 and a light mixer second area 500B2. The diffusion sheet 600 includes a first diffusion sheet 600W1 and a second diffusion sheet 600W2. The first diffusion sheet 600W1 is disposed in the light mixer first area 500B1 and near the exit thereof, and the second diffusion sheet 600W2 is disposed in the light mixer second area 500B2 and near the exit thereof. The light mixer first area 500B1 is configured to receive the light beam from the first area 400R1, and the first diffusion sheet 600W1 in the light mixer first area 500B1 near the exit prevents the light beam received by the light mixer first area 500B1 from being emitted directly, so that the light beam is multiplexed and evenly mixed, and then emitted. The light mixer second area 500B2 is configured to receive the light beam from the second area 400R2, and the second diffusion sheet 600W2 in the light mixer second area 500B2 near the exit prevents the light beam received by the light mixer second area 500B2 from being emitted directly, so that the light beam is multiplexed and evenly mixed, and then emitted. In this case, the light mixer first area 500B1 or the light mixer second area 500B2 may be an integrating sphere or an integrating rod, but the disclosure is not limited hereto.

In the embodiment, the controller 700 is electrically connected to the array optical switch 400. The controller 700 controls the array optical switch 400, so that the light mixer first area 500B1 outputs a first color light C1, and the light mixer second area 500B2 outputs a second color light C2. That is to say, the controller 700 controls whether the switch in the array optical switch 400 should be turned on or off, so that the spectral light beam incident on the corresponding position of the optical switch that is turned on passes through. Therefore, the passing light beam is prevented by the first diffusion sheet 600W1 or the second diffusion sheet 600W2 near the exit in the light mixer first area 500B1 or the light mixer second area 500B2, so that the light beam is multiplexed and evenly mixed, and then emitted to form the first color light C1 or the second color light C2.

In an embodiment, the controller 700 includes, for example, a central processing unit (CPU), a microprocessor, a digital signal processor (DSP), a programmable controller, a programmable logic device (PLD), or other similar devices or a combination of the devices, and is not limited by the disclosure. In addition, in an embodiment, each function of the controller 700 may be implemented as multiple codes. The codes are stored in a memory unit and are executed by the controller 700. Alternatively, in an embodiment, each function of the controller 700 may be implemented as one or more circuits. The disclosure does not limit how each function of the controller 700 is implemented by means of either a software or a hardware.

In an embodiment, in addition to controlling whether each optical switch is turned on, the controller 700 also controls the intensity of the spectral light passing through each optical switch. That is to say, the controller 700 controls the intensity of the first area reflected light beam R1 or the second area reflected light beam R2 passing through the array optical switch 400.

Figure 2:
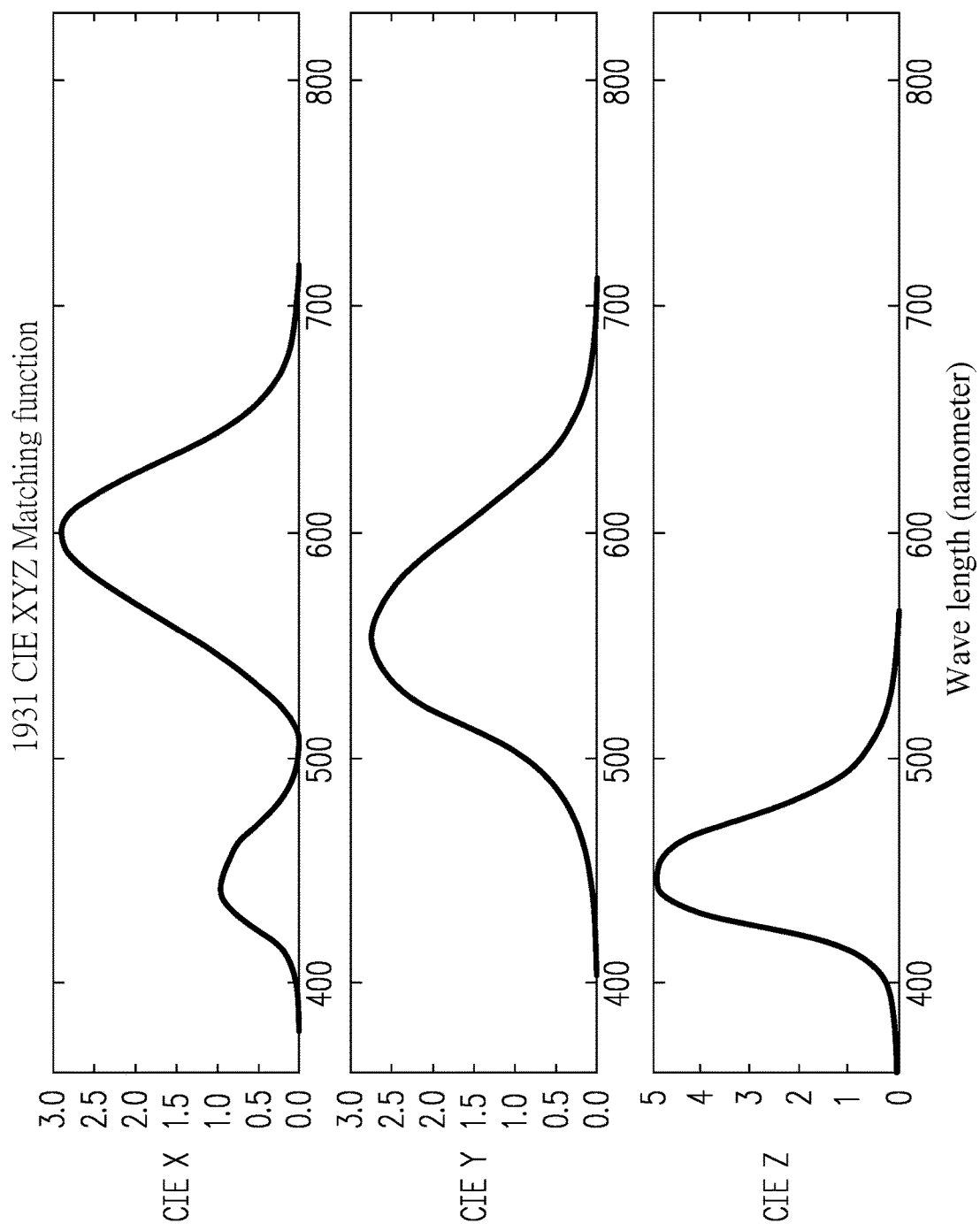
FIG. 2 is a graph illustrating a response curve as an X, Y or Z matching function of a standard chromaticity space.

FIG. 2 is a graph illustrating a response curve as an X, Y or Z matching function of a standard chromaticity space. Referring to FIG. 2, the X matching function of the standard chromaticity space perceived by the human eye as the visible light spectrum is taken as an example. The controller 700 controls the optical switch that should be turned on in the array optical switch 400 and the light intensity that the optical switch should output, so that the spectrum of the first area reflected light beam R1 or the second area reflected light beam R2 after passing through the controller 700 is substantially the same as the X matching function of the standard chromaticity space. That is to say, the corresponding response curve turned on by the controller 700 controlling the array optical switch 400 is the X matching function of the standard chromaticity space. However, the disclosure is not limited thereto, and the aforementioned response curve may be an X, Y, Z matching function, or the other color light of a standard chromaticity space, or a combination thereof.

In the embodiment, for example, the first color light C1 may be the color light combined by the X, Y, Z matching functions, or the other color light of the standard chromaticity space; C2 may have the different color with the first color light C1. If the test subject is unable to distinguish the color of the first color light C1 from the color of the second color light C2, the test subject may have a weaker ability to distinguish the two different colors. The controller 700 is then used to sequentially modulate with different spectral combination to distinguish the first color light C1 and the second color light C2, and the spectral combination of the inspection result is used by the test subject as a reference value for a color-resolving corrector, in which the corrector is, for example, an optical filtering film on the surface of the spectacles.

In the embodiment, the color-light generation system 10 further includes a reflective surface concentrator 200. The reflective surface concentrator 200 is disposed at the light exit of the light source 100 and is configured to concentrate the first area light beam L1 or the second area light beam L2 before transmitting the first area light beam L1 or the second area light beam L2 to the reflective grating 300.

Based on the above, in the color-light generation system 10 of an embodiment of the disclosure, the array optical switch 400 is designed to include the first area 400R1 and the second area 400R2. The light mixer 500 is divided into the light mixer first area 500B1 and the light mixer second area 500B2. The light mixer first area 500B1 is configured to receive the light beam from the first area 400R1, and the first diffusion sheet 600W1 in the light mixer first area 500B1 near the exit prevents the light mixer first area 500B1 from receiving the direct light beam, so that the light beam is multiplexed and evenly mixed, and then emitted. The light mixer second area 500B2 is configured to receive the light beam from the second area 400R2, and the second diffusion sheet 600W2 in the light mixer second area 500B2 near the exit prevents the light mixer second area 500B2 from receiving the direct light beam, so that the light beam is multiplexed and evenly mixed, and then emitted, and the light mixer first area 500B1 outputs the first color light C1, and the light mixer second area 500B2 outputs the second color light C2. Therefore, compared to a color-light generation system that is integrated using multiple sets of color generators, the color-light generation system 10 of the embodiment of the disclosure reduces the number of optical elements used in the system, which leads to a reduced cost. Moreover, the color-light generation system 10 uses only the controller 700 to modulate the inspection light (that is, the first color light C1 and the second color light C2) that the test subject sees, so that the cost of the color-light generation system 10 is further reduced.

In the color-light generation system 10 of the embodiment of the disclosure, the optical path of the first area light beam L1 and the second area light beam L2 are designed so that the first area reflected light beam R1 and the second area reflected light beam R2 are respectively incident on different areas of the array optical switch 400. Therefore, the light intensity of the first color light C1 and the second color light C2 output by the color-light generation system 10 is relatively high, which improves the reliability of the inspection result of the test subject. The color-light generation system 10 adopts the reflective surface concentrator 200, so that the light energy output by the light source 100 is converted into the first color light C1 and the second color light C2 at a relatively high ratio. Therefore, the light energy of the color-light generation system 10 is utilized at a higher rate.

Figure 3:
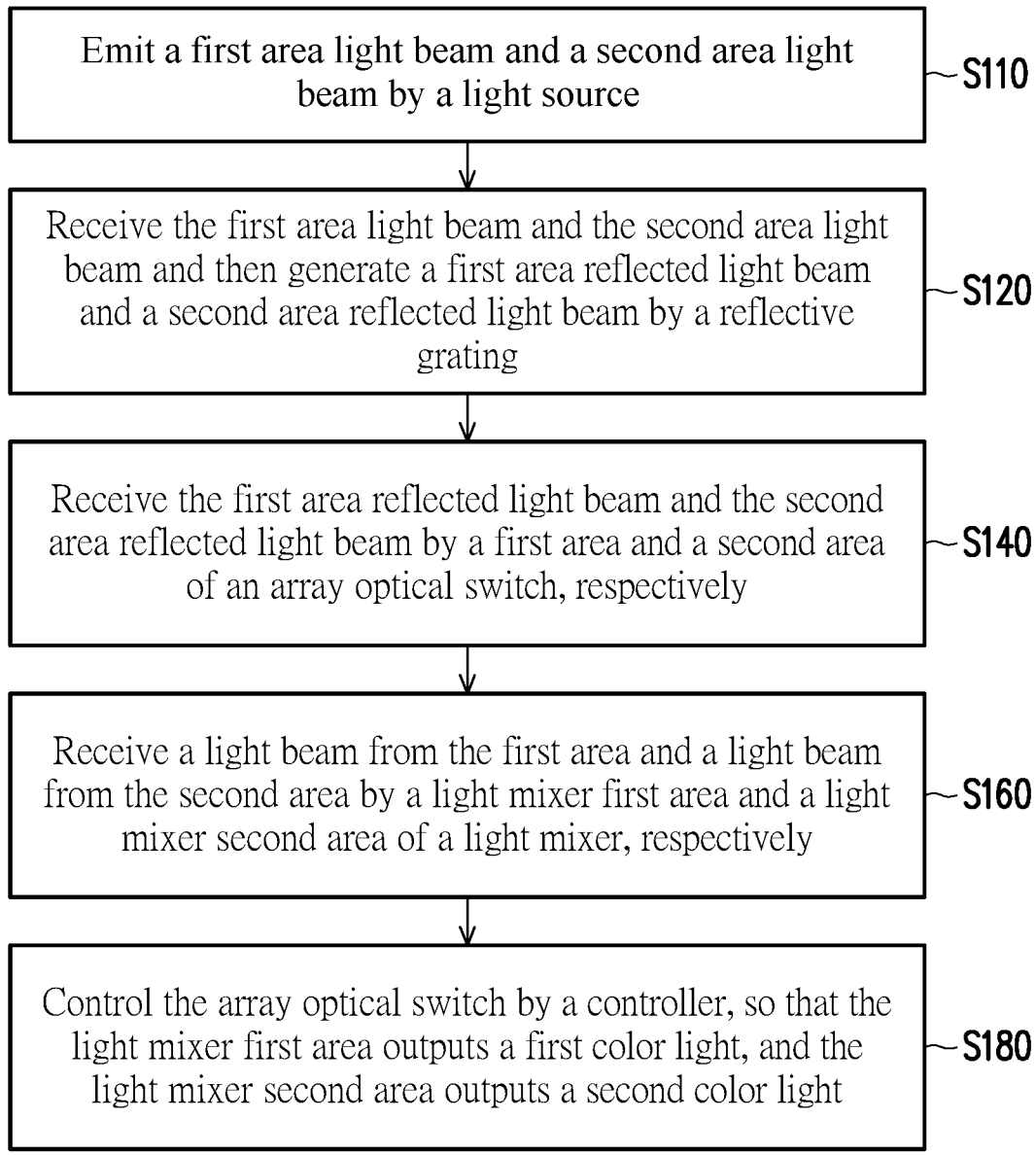
FIG. 3 is a flowchart of a method of using a color-light generation system according to an embodiment of the disclosure.

FIG. 3 is a flowchart of a method of using a color-light generation system according to an embodiment of the disclosure. Referring to FIG. 3, an embodiment of the disclosure provides a method of using the color-light generation system 10, which includes the following steps. In step S110, the first area light beam L1 and the second area light beam L2 is emitted by the light source 100. In step S120, the first area reflected light beam R1 and the second area reflected light beam R2 are generated after the first area light beam L1 and the second area light beam L2 are received by the reflective grating 300. In step S140, the first area reflected light beam R1 and the second area reflected light beam R2 are received by the first area 400R1 and the second area 400R2 of the array optical switch 400, respectively. In step S160, the light mixer 500 is divided into a first area 500B1 and a second area 500B2, the light beam from the first area 400R1 and the light beam from the second area 400R2 are received by the light mixer first area 500B1 and the light mixer second area 500B2 of the light mixer 500, respectively. The light mixer first area 500B1 is prevented by the first diffusion sheet 600W1 in the light mixer first area 500B1 close to the exit from directly receiving the light beam, so that the light beam is multiplexed and evenly mixed, and then emitted. The light mixer second area 500B2 is prevented by the second diffusion sheet 600W2 in the light mixer second area 500B2 close to the exit from directly receiving the light beam, so that the light beam is multiplexed and evenly mixed, and then emitted. In step S180, the controller 700 is configured to control the array optical switch 400, so that the light mixer first area 500B1 outputs the first color light C1, and the light mixer second area 500B2 outputs the second color light C2.

Figure 4:
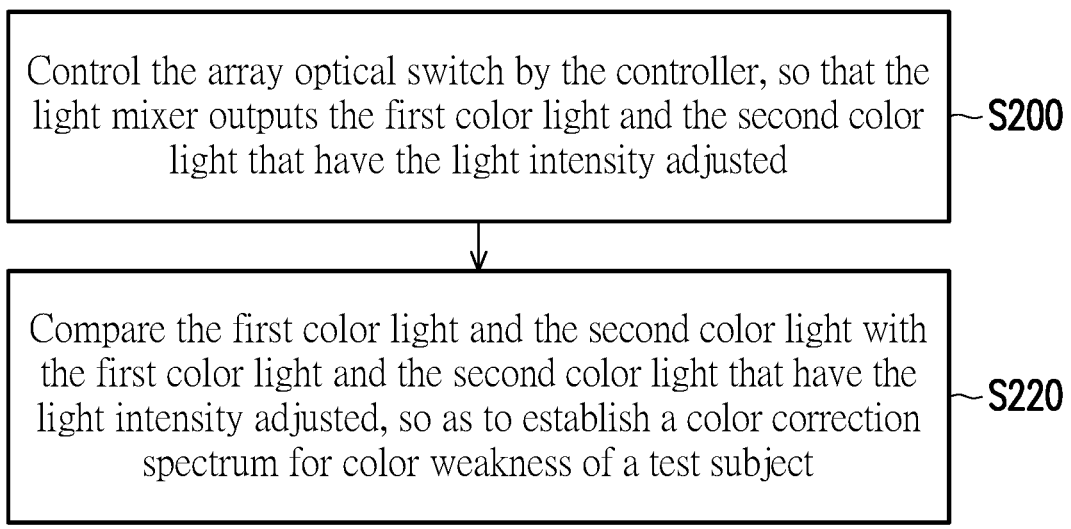
FIG. 4 is a flowchart according to a method of using a color-light generation system of an embodiment of the disclosure which establishes a color correction spectrum for color weakness of a test subject.
Figure 5A:
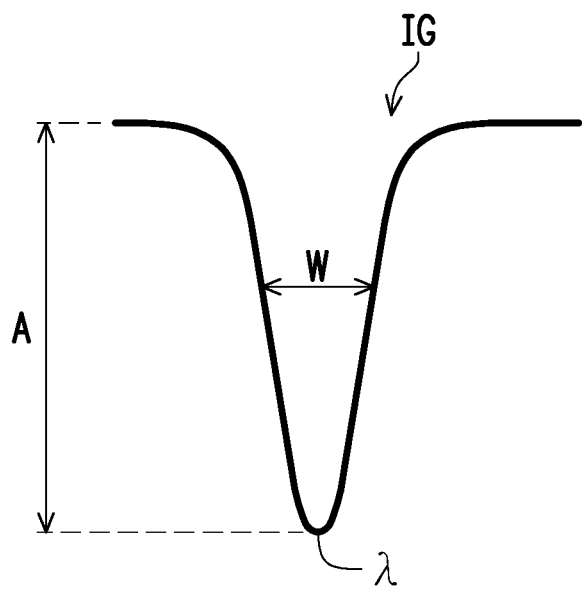
FIG. 5A is a schematic graph of an inverse Gaussian function.
Figure 5B:
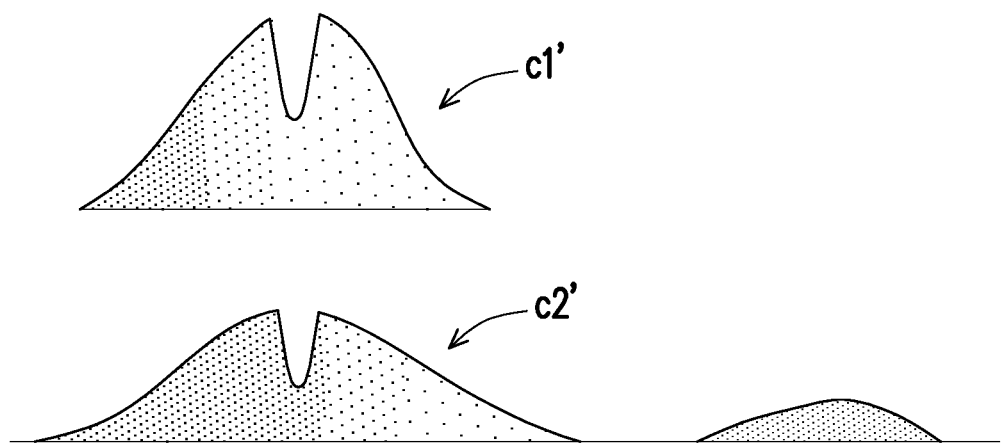
FIG. 5B is a schematic graph of a first color light and a second color light adjusted according to a method of using a color-light generation system of an embodiment of the disclosure which establishes a color correction spectrum for color weakness of a test subject.

FIG. 4 is a flowchart according to a method of using a color-light generation system of an embodiment of the disclosure which establishes a color correction spectrum for color weakness of a test subject. FIG. 5A is a schematic graph of an inverse Gaussian function. FIG. 5B is a schematic graph of a first color light and a second color light adjusted according to a method of using a color-light generation system of an embodiment of the disclosure which establishes a color correction spectrum for color weakness of a test subject. Referring to FIG. 4 and FIG. 5A to FIG. 5B, in the embodiment, the method of using the color-light generation system 10 further includes the following steps. In step S200, the array optical switch 400 is controlled by the controller 700, so that the first color light C1 and the second color light C2 that have the light intensity adjusted are output by the light mixer 500. In step S220, the first color light C1 and the second color light C2 are compared with the first color light C1 and the second color light C2 that have the light intensity adjusted, so as to establish the color correction spectrum for color weakness of the test subject. In this case, the above-mentioned step S220 includes the following: adjusting an attenuation intensity A, a full width at half maximum (FWHM) W, or a wave length λ of the inverse Gaussian (IG) function, and multiplying the inverse Gaussian function IG by the function of the first color light C1 and the second color light C2 to generate the adjusted first color light C1' and the second color light C2', so that the test subject adjusts from being unable to distinguish the color, to being able to distinguish the color. The attenuation intensity A, for example, falls within the range of 0% to 100%. The full width at half maximum (FWHM) W, for example, falls within the range of 0 nm to 150 nm. The wave length λ, for example, falls within the range of 400 nm to 700 nm. That is to say, the color-light generation system 10 can inspect a test subject's ability to distinguish the color. When it is shown that the test subject has color weakness and a defect in the ability to distinguish the color, the color-light generation system 10 is adjusted to adjust the light intensity of the output color light C1 and color light C2 to the extent where the test subject has the ability to distinguish the color. From the variation of being unable to distinguish the light intensity of the color light C1 and the color light C2, to being able to distinguish the light intensity of the color light C1 and the color light C2, the color correction spectrum for color weakness of the test subject can be measured without requiring a filter to adjust the intensity output of the color light C1 and the color light C2.

To sum up, in the color-light generation system of an embodiment of the disclosure, the array optical switch is designed to include the first area and the second area, and the light mixer first area and the light mixer second area output the first color light and the second color light corresponding to the first area and the second area of the array optical switch, respectively. Therefore, compared to a color-light generation system that is integrated using multiple sets of color generators, the color-light generation system of the embodiment of the disclosure reduces the number of optical elements used in the system, which leads to a reduced cost. Moreover, the color-light generation system uses only the controller to modulate the inspection light that the test subject sees, so that the cost of the color-light generation system is further reduced.

What is claimed is:
1. A color-light generation system, comprising:
a light source, configured to emit a first area light beam and a second area light beam;
a reflective grating, configured to receive the first area light beam and the second area light beam and then generate a first area reflected light beam and a second area reflected light beam;
an array optical switch, comprising a first area and a second area, wherein the first area and the second area are configured to receive the first area reflected light beam and the second area reflected light beam, respectively;
a light mixer, comprising a light mixer first area and a light mixer second area, wherein the light mixer first area receives a first light beam from the first area, the light mixer second area receives a second light beam from the second area, the first light beam reflects inside the light mixer first area, and the second light beam reflects inside the light mixer second area; and
a controller, electrically connected to the array optical switch,
wherein the controller controls the array optical switch, so that the light mixer first area outputs a first color light, and the light mixer second area outputs a second color light.

2. The color-light generation system according to claim 1, wherein a spectrum of the first color light and a spectrum of the second color light are different.

3. The color-light generation system according to claim 1, wherein the reflective grating is a concave grating.

4. The color-light generation system according to claim 1, further comprising:
a reflective surface concentrator, disposed at a light exit of the light source and configured to concentrate and then transmit the first area light beam or the second area light beam to the reflective grating.

5. The color-light generation system according to claim 1, further comprising:
a diffusion sheet, comprising a first diffusion sheet and a second diffusion sheet, wherein the first diffusion sheet is disposed in the light mixer first area and close to an exit thereof, and the second diffusion sheet is disposed in the light mixer second area and close to an exit thereof.

6. A method of using a color-light generation system, comprising:
emitting a first area light beam and a second area light beam by a light source;
receiving the first area light beam and the second area light beam and then generating a first area reflected light beam and a second area reflected light beam by a reflective grating;
receiving the first area reflected light beam and the second area reflected light beam by a first area and a second area of an array optical switch, respectively;
receiving a first light beam from the first area and a second light beam from the second area by a light mixer first area and a light mixer second area of a light mixer, respectively, wherein the first light beam reflects inside the light mixer first area, and the second light beam reflects inside the light mixer second area; and
controlling the array optical switch by a controller, so that the light mixer first area outputs a first color light, and the light mixer second area outputs a second color light.

7. The method of using the color-light generation system according to claim 6, further comprising:
controlling the array optical switch by the controller, so that the light mixer outputs the first color light and the second color light that have a light intensity adjusted; and
comparing the first color light and the second color light with the first color light and the second color light that have the light intensity adjusted, so as to establish a color correction spectrum for color weakness of a test subject.

8. The method of using the color-light generation system according to claim 7, wherein comparing the first color light and the second color light with the first color light and the second color light that have the light intensity adjusted, so as to establish the color correction spectrum for color weakness of the test subject comprises:
adjusting an attenuation intensity, a full width at half maximum (FWHM) or a wave length of an inverse Gaussian function, and multiplying the inverse Gaussian function by a function of the first color light and the second color light to generate an adjusted first color light and an adjusted second color light, so that the test subject adjusts from being unable to distinguish a color, to being able to distinguish the color.

9. The method of using the color-light generation system according to claim 8, wherein
the attenuation intensity falls within a range of 0% to 100%;
the full width at half maximum (FWHM) falls within a range of 0 nm to 150 nm; and
the wave length falls within a range of 400 nm to 700 nm.

10. The method of using the color-light generation system according to claim 6, wherein a spectrum of the first color light and a spectrum of the second color light are different.

11. The method of using the color-light generation system according to claim 6, wherein the reflective grating is a concave grating.

12. The method of using the color-light generation system according to claim 6, further comprising:
concentrating and then transmitting the first area light beam or the second area light beam to the reflective grating by a reflective surface concentrator.

* * * * *